US011459542B2

(12) United States Patent
Loskill et al.

(10) Patent No.: US 11,459,542 B2
(45) Date of Patent: Oct. 4, 2022

(54) MICRO-PHYSIOLOGICAL ORGANOID CULTURE

(71) Applicant: EBERHARD KARLS UNIVERSITÄT TÜBINGEN, Tübingen (DE)

(72) Inventors: Peter Loskill, Stuttgart (DE); Christopher Probst, Stuttgart (DE); Stefan Liebau, Rangendingen (DE); Kevin Achberger, Tübingen (DE); Jasmin Haderspeck, Tübingen (DE)

(73) Assignee: EBERHARD KARLS UNIVERSITÄT TÜBINGEN, Tübingen (DE)

( * ) Notice: Subject to any disclaimer, the term of this patent is extended or adjusted under 35 U.S.C. 154(b) by 383 days.

(21) Appl. No.: 16/753,047

(22) PCT Filed: Oct. 1, 2018

(86) PCT No.: PCT/EP2018/076645
§ 371 (c)(1),
(2) Date: Apr. 2, 2020

(87) PCT Pub. No.: WO2019/068640
PCT Pub. Date: Apr. 11, 2019

(65) Prior Publication Data
US 2020/0239843 A1    Jul. 30, 2020

(30) Foreign Application Priority Data

Oct. 5, 2017    (DE) .................... 10 2017 217 738.1

(51) Int. Cl.
*C12N 5/079* (2010.01)
*C12M 3/00* (2006.01)
*C12M 1/12* (2006.01)

(52) U.S. Cl.
CPC .......... *C12N 5/0621* (2013.01); *C12M 21/08* (2013.01); *C12M 25/02* (2013.01); *C12N 2502/1323* (2013.01); *C12N 2502/1335* (2013.01); *C12N 2502/28* (2013.01); *C12N 2513/00* (2013.01); *C12N 2533/80* (2013.01)

(58) Field of Classification Search
None
See application file for complete search history.

(56) References Cited

PUBLICATIONS

Laura C. Bahlmann et al. Dynamic bioengineered hydrogels as scaffolds for advanced stem cell and organoid culture1 MRS Communications. vol. 7, No. 03, Aug. 29, 2017 (Aug. 29, 2017), pp. 472-486 DOI: 10.1557/mrc.2017.72 ISSN: 2159-6859, XP055523881.
Kevin S. Jackson et al. "Three-Dimensional Ovarian Organ Culture as a Tool to Study Normal Ovarian Surface Epithelial Wound Repair" Endocrinology. US. vol. 150. No. 8, Aug. 1, 2009 (Aug. 1, 2009), pp. 3921-3926 DOI: 10.1210/en.2008-1674 ISSN: 0013-7227, XP055523875.

(Continued)

*Primary Examiner* — Teresa E Knight
(74) *Attorney, Agent, or Firm* — Harness, Dickey & Pierce, P.L.C.; Stephen T. Olson

(57) ABSTRACT

The present invention is in the field of the cultivation of biological cells and tissues with organ-like function on a microphysiological scale and provides a method for the microphysiological co-cultivation of 3D organoid tissue and at least one 2D cell layer.

16 Claims, 3 Drawing Sheets

(56) References Cited

PUBLICATIONS

Figure 1:
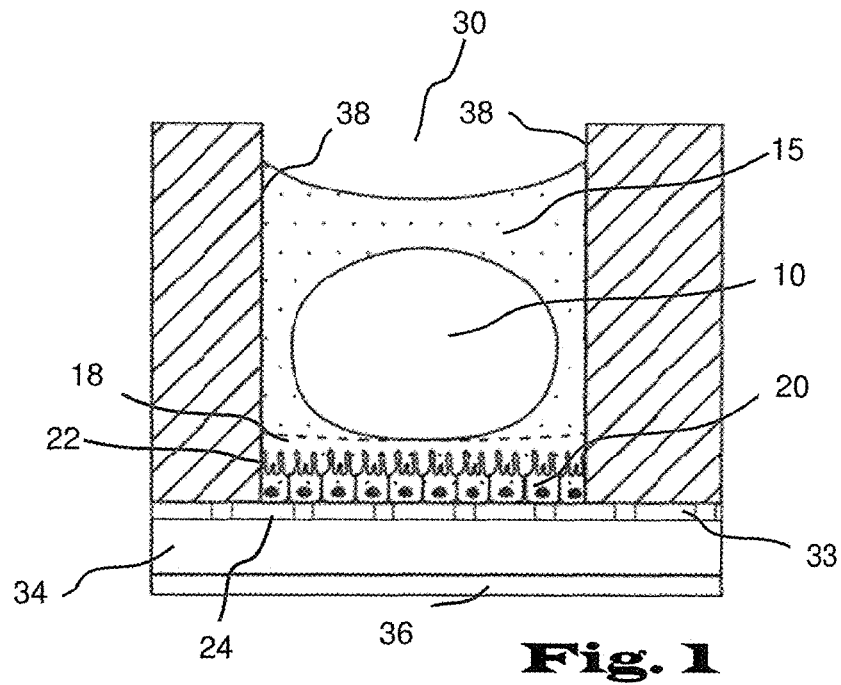

M. A. Lancaster et al. "Organogenesis in a dish: Modeling development and disease using organoid technologies" *Science*. vol. 345, No. 6194. Jul. 17, 2014 (Jul. 17, 2014), pp. 283,1-9 DOI: 10.1126/science. 1247125 ISSN: 0036-8075, XP055130123.

Dodson, Kirsten II et al. "Retina-on-a-chip: a microfluidic platform for point access signaling studies" *Biomedical Microdevices, Kluwer. Dordrecht. NL*, vol. 17, No. 6, Nov. 11, 2015 (Nov. 11, 2015), pp. 1-10, [retrieved on Nov. 11, 2015] DOI: 10.1007/S 10544-015-0019-X ISSN: 1387-2176, XP035902050.

Julia Rogal et al. "Integration concepts for multi-organ chips: how to maintain flexibility?!" *Future Science OA*. vol. 3, No. 2, May 1, 2017 (May 1, 2017), p. ESC) 180 DOI: 10.4155/fsoa-2016-0092 XP055527584.

Llonch, Silvia et al. "Organoid technology for retinal repair" *Developmental Biology*. vol. 433, No. 2, Dec. 25, 2017 (Dec. 25, 2017), pp. 132-143 DOI: 10.1016/J.YDBI0.2017.09.028 ISSN: 0012-1606. XP085322057.

Haderspeck J., Acberger K., Probst C.. Rogal J., et al. "Development of a 3-dimensional microphysiological Retina-on-a-chip system." *Investigative Ophtalmology & Visual Science*. vol. 59. No. 9, Apr. 29, 2018. Revised May 3, 2018., Retrieved from the Internet: <https://iovs.arvojournals.org/article.aspx7article>id=2689245 [retrieved on Nov. 20, 2018] XP002786886.

Christopher Probst et al. "Iligh-throughput organ-on-a-chip systems: Current status and remaining challenges" *Current Opinion in Biomedical Engineering*. vol. 6, Jun. 1, 2018 (Jun. 1, 2018), pp. 33-41 DOI: 10.1016/j.cobme.2018.02.004 ISSN: 2468-4511, XP055523859.

Völkner et al. "Retinal Organoids from Pluripotent Stem Cells Efficiently Recapitulate Retinogenesis", *Stem Cell Reports*, vol. 6, 525-538, Apr. 12, 2016.

International Search Report (in English and German) and Written Opinion of the ISA (in German) issued in PCT/EP2018/076645, dated Jan. 10, 2019; ISA/EP.

MICRO-PHYSIOLOGICAL ORGANOID CULTURE

CROSS-REFERENCE TO RELATED APPLICATIONS

This application is a 371 U.S. National Phase of International Application No. PCT/EP2018/076645, filed Oct. 1, 2018, which claims the benefit of German Patent Application No. 10 2017 217 738.1, filed Oct. 5, 2017. The entire disclosures of the above applications are incorporated herein by reference.

DESCRIPTION

The present invention is in the field of the cultivation of biological cells and tissues with organ-like function on a microphysiological scale and provides a method for the microphysiological co-cultivation of 3D organoid tissue and at least one 2D cell layer.

Cell and stem cell-based in vitro models are being developed which, on the other hand, can replace ethically problematic and cost-intensive animal models in the research of genetic or idiopathic diseases of the human body and in the development of prophylactic and therapeutic agents.

Microphysiological (MPS) or so-called "Organ-on-a-Chip" (OoaC) systems enable the cultivation of endogenous cells such as cell lines, primary cells, cells of an embryonic origin or induced pluripotent stem cells (iPSZ) under physiological conditions in order to reconstruct specific tissues such as lungs, heart, intestines and kidneys. Complex stem cell-based organ systems from several cell types have been developed, so-called organoids. These arise largely independently during in vitro differentiation and self-organizingly under the influence of fewer external signaling molecules. Examples of this are pancreatic, intestinal, brain or retinal organoids. To a certain extent, they are able to simulate physiological relationships, since they combine to form complex cell assemblies in a self-organizing manner. For example, patient-specific in vitro organoid systems can be made available from a patient's own stem cells (individualized iPS cells), in particular those useful for the development of individualized therapy, screening for drug effects and drug safety, or for researching the basics of diseases and physiological relationships in the organ systems.

The disadvantage is that there is currently no vascular supply in the cultivation of such organoids and in particular there is no guarantee of development of the organoids beyond a certain level of embryonic maturity, nor can interaction with cell types not contained in the organoid or when such cell types are in unphysiological cell orientations. Thus, in known cultivation processes, deficient supply, cell death and unphysiological conditions presumably occur due to a lack of supply and interaction, which complicates the usefulness of the findings found in vitro.

Particularly promising organoid systems include so-called retina organoids which are intended to make the complex interactions in the multilayered retina simulable. Retina organoids can be obtained from patient-specific iPS cells in particular, and include all cell types of the neural retina: Photoreceptors, retinal neurons and glial cells, in a complex interplay similar to an embryonic situation. The prophylaxis and therapy of common and severe diseases of the retina, such as age-related macular degeneration (AMD) or retinitis pigmentosa (RP), which are the main causes of blindness in humans, are an important motivation for the development of the most physiological retinal organ systems possible. However, to model a retina that is as physiological as possible, the current retina organoid systems lack a) intercellular interaction of the photoreceptors (especially the outer segments thereof) with retinal pigment epithelial cells (RPE), b) integration of subpigment epithelial endothelial cells and vessels of the choroidea and c) a physiological extracellular matrix (EZM), especially in the interaction area of the RPE, i.e. the so-called interphotoreceptor matrix.

The present invention was based on the technical problem of providing methods and agents for improved cultivation of organ-like organ systems for the research and development of prophylactic or therapeutic agents from patient-specific cells in particular, primarily iPS cells, which have the disadvantages mentioned of known organoid cultures, in particular incomplete maturation, cell death and overcoming a lack of cell interaction.

The technical problem is completely solved by a method for the co-cultivation of organoid tissue in a bioreactor vessel with a semi-permeable membrane on the bottom, in particular on a micro-physiological scale. The process contains at least the following steps: Step (a): seeding cells of at least one first cell type in the bioreactor vessel onto the membrane, step (b): culturing these seeded cells so that a 2D cell layer, in particular a confluent, supported 2D cell layer, forms on the membrane, and in particular immediately thereafter step (c): introducing the organoid, which contains cells of at least two further cell types which are arranged in a defined 3D structure relative to one another, and hydrogel into the bioreactor vessel (30) and onto the supported 2D cell layer (20), specifically with the proviso that the organoid in the bioreactor vessel into which it is introduced is kept at a defined distance from the supported 2D cell layer by the hydrogel which has also been introduced previously and/or at the same time. This distance preferably corresponds to the dimensions between the interacting cells in vivo; this is explained in more detail below.

The invention therefore particularly provides for a 3D organoid with a 3D structure of a plurality of cell types to be positioned at a defined distance above at least one 2D cell layer, that is to say in particular a monolayer, which is made of cells of at least one further cell type. This enables controllable, physiologically adequate interactions between at least one cell type of the 3D organoid and the at least one further cell type of the 2D monolayer disposed underneath. A physiologically adequate supplying of the cells of the 3D organoid above the underlying 2D monolayer is also possible, if necessary. This makes it possible to cultivate, under physiologically adequate conditions, the organoid provided; improved maturation and differentiation of the organ tissue is achieved and unwanted cell death is avoided. A stable interaction between the 3D organoid and the 2D cell layer can advantageously be achieved and consequently investigated, so that an organ-typical sandwich culture which reflects the complex structure and function of in vivo organs is obtained.

In a preferred variant it is provided that in step (c) there is the further requirement that the organoid in the bioreactor vessel is additionally also spaced from away from the walls of the bioreactor vessel by way of the hydrogel introduced. In accordance with this preferred variant, the introduced organoid hovers, as it were, in the bioreactor vessel without mechanical contact with the vessel walls and at a defined, that is to say controllable or predeterminable, distance from the at least one 2D cell layer located therebelow. This allows a further improvement in the results of cultivating the organoid: There is less cell death, and the self-organizing structuring of the cell types within the organoid continues in the course of the cultivation in the direction of an adult, that is to say largely fully developed stratification and structure of the cells contained.

In order to enable the spacing of the 3D organoid from the 2D cell layer in the bioreactor vessel according to the invention, a first variant provides that in step (c) the organoid is introduced into the bioreactor vessel together with the hydrogel. It is particularly provided that the organoid is poured or pumped into the vessel and onto the supported 2D cell layer in a defined volume of hydrogel, which is initially in the liquid phase, and the hydrogel cures there while the organoid is floating in the hydrogel and thereby hovers at a defined distance above the 2D cell layer and is optionally also spaced from the walls of the vessel. The desired defined distance is determined in particular by the time profile of the transition (curing) from the liquid to the solid phase of the hydrogel introduced in step (c) in connection with its viscosity. The viscosity determines the time the organoid takes to sink in the hydrogel towards the underlying 2D cell layer. If the hydrogel cures, further sinking of the organoid is prevented and a predeterminable distance to the 2D cell layer is reached.

In an alternative variant it is provided that step (c) contains substeps, namely at least a first substep (c1) of: introducing some of the hydrogel, preferably as a liquid sol and associated hardening to form a gel, initially in order to form a defined hydrogel spacer layer relative to the 2D cell layer, and then a second substep (c2) of: introducing the organoid onto the hydrogel spacer layer formed, preferably in hydrogel as a liquid sol and, in connection therewith, hardening to a gel in order to fix the organoid in the vessel, optionally also spaced from the walls of the vessel.

The desired defined distance is determined in particular by the amount/volume of the hydrogel fraction introduced in step (c1).

In a preferred embodiment, it is also provided that during cultivation, the at least one 2D cell layer supported on the membrane is perfused at its basal pole, that is to say the side facing away from the organoid, separately from its apical pole, that is to say the side facing the organoid. This creates an adequate physiological supply of the cultivated organoid through the at least one 2D cell layer. Furthermore, an adequate physiological function of the at least one 2D cell layer can be achieved, especially if it forms or is intended to form polarization in the apical and basal poles. This is advantageously associated with an adequate physiological interaction of the 2D cell layer with the organoid. In this way, an optimally improved in vitro organoid system can be provided which largely simulates the physiological states and functions of the organ in vivo.

The invention accordingly also relates to an in vitro tissue culture which can be produced using the method according to the invention. According to the invention, this in vitro tissue culture is contained in a bioreactor vessel with a semipermeable membrane on the bottom, and preferably contains or consists of: at least one 2D cell layer containing at least one first cell type, supported on the semipermeable membrane, an organoid containing cells of at least two further cell types arranged in a defined 3D structure with respect to one another, and hydrogel in which the organoid is embedded in the bioreactor vessel and which is arranged at a defined distance from the supported 2D cell layer and is preferably also spaced from the walls of the bioreactor vessel.

In preferred variants, the defined distance of the organoid from the 2D cell layer is from 1 to 200 µm, preferably from 1 to 100 µm, more preferably from 2 to 20 µm, particularly preferably 2 to 15 µm.

All cells can be of human or animal origin; mouse and rat are preferred. The cells can be obtained from embryonic or preferably alternatively from induced pluripotent stem cells (iPS). They can have been taken from embryonic or adult tissue; human embryonic cells are preferably excluded.

In a special embodiment of the in vitro tissue culture, the at least one first cell type of the 2D cell layer is selected from: epithelial cells, pigment epithelial cells or epithelial-like cell lines, such as ARPE-19; endothelial cells; stromal cells containing fibrocytes and/or fibroblasts; and muscle cells containing myoblasts, myocytes and/or muscle fibers. Epithelial cells are particularly preferred, preferably in combination with endothelial cells, a first 2D cell layer containing and preferably consisting of epithelial cells being arranged on the upper side of the membrane facing the organoid. A further 2D cell layer, which contains endothelial cells and preferably consisting thereof, is particularly preferably arranged on the underside of the membrane which faces away from the organoid. In a preferred variant, human embryonic cells, in particular embryonic stem cells as such, are excluded as cell types of the 2D cell layers, so that the 2D cell layers are free of such cells.

The organoid is preferably selected from the group of self-organizing or multi-cell type tissues with a defined 3D structure that can be produced by cell pressure. This group preferably contains retina organoids, brain organoids, pancreatic organoids, and intestinal organoids or preferably consists exclusively of them. In a preferred variant, human embryonic cells, in particular embryonic stem cells as such, are excluded as cells of the 3D organoid, and the organoid is thus free of such cells.

In a particularly preferred embodiment of the in vitro tissue culture, the organoid is a retina organoid which contains at least photoreceptor cells and cells of at least one other cell type of the neural vertebrate retina. In this version, the supported 2D cell layer is a confluent monolayer made of retinal pigment epithelial cells. Another 2D cell layer, which consists of endothelial cells, is preferably arranged on the underside of the membrane facing away from the organoid.

The invention also relates to the use of the co-cultivation method according to the invention and the in vitro tissue culture according to the invention for the development and/or selection of prophylactic and/or therapeutic agents and active substances, in particular in patient-specific prophylactic and/or therapeutic methods, especially in individualized therapy. This method preferably provides for the recovery of 3D organoid and in particular also the at least one 2D cell layer from isolated cells of the patient, in particular from iPS cells.

The invention is illustrated by the figures and the following examples:

FIG. 1 shows a schematic sectional view of a first embodiment of the bioreactor system with a bioreactor vessel (30) on a support (36) with a semipermeable membrane (33) on the bottom. Disposed therein is the in vitro tissue culture cultivated according to the invention, consisting of a 3D organoid (10) which is co-cultivated with at least one, preferably single-layer 2D cell layer (20) arranged at a defined distance therefrom and supported on the membrane (33). The organoid (10) in the bioreactor vessel (30) hovers over the 2D cell layer (20) therebelow. In the embodiment shown, the 2D cell layer (20) is a confluent cell layer made of epithelial cells. The apical pole (22) of the cell layer points in the direction of the organoid, the basal pole (24) points in the opposite direction; in the embodiment shown, it rests on the membrane (33). A basal perfusion channel (34) is provided in the bioreactor system and allows perfusion of the basal pole (24) of the 2D cell layer (20). The carrier (36) is preferably a transparent substrate, a glass sample slide for enabling examination by transmitted light microscopy.

Figure 2:
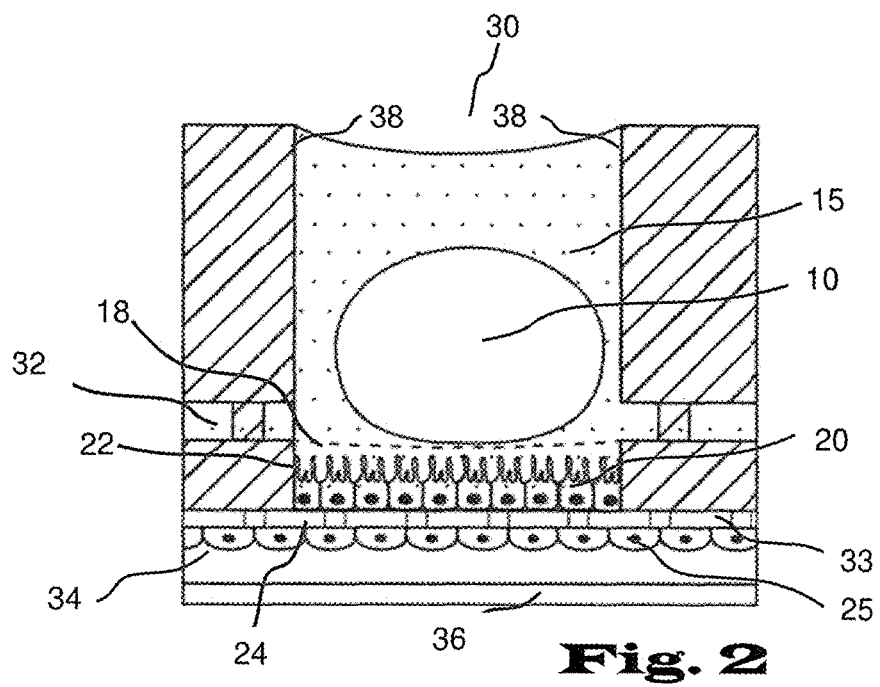

FIG. 2 shows a schematic sectional view of a variant of the embodiment of the bioreactor system according to FIG. 1. The semipermeable membrane (33) has a first 2D cell layer (20) on the side facing the organoid and a second 2D cell layer (25) on the opposite, basal side. In the embodiment shown, the first 2D cell layer (20) is a confluent cell layer made of epithelial cells; the second 2D cell layer (25) is a confluent cell layer made of endothelial cells. Perfusion of the basal pole (24) of the 2D cell layer (20) is made possible via the basal perfusion channel (34). An additional apical perfusion channel (32) allows separate perfusion of the apical side of the 2D cell layer (20) and the organoid (10).

Figure 3:
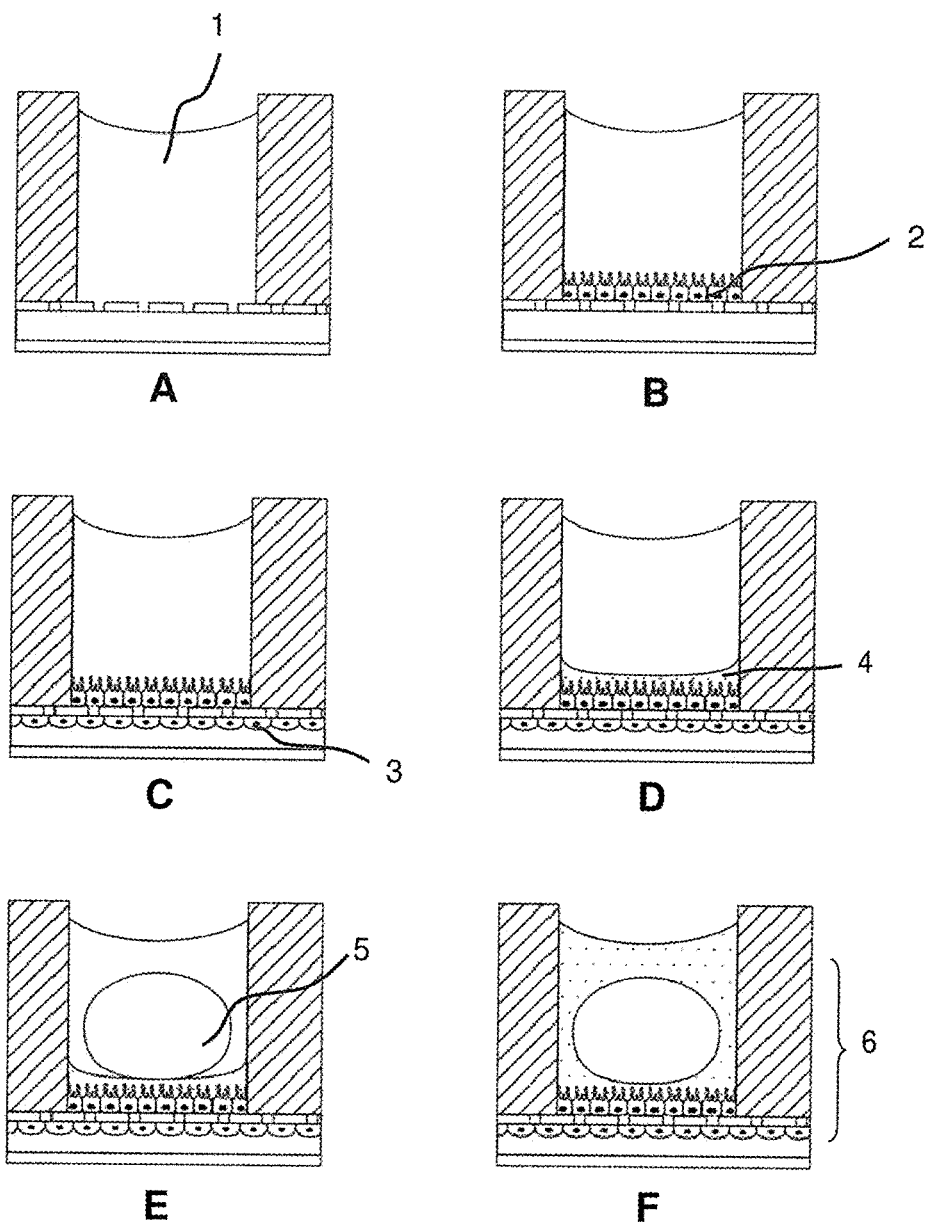

FIG. 3 shows, in accordance with the schematic representations in FIGS. 1 and 2, the colonization phases of the bioreactor system and cultivation of the in vitro tissue formed using a retina organoid (RO) in co-culture with retinal pigment epithelium (RPE) and endothelial layer (EN): In step A, a bioreactor vessel with a semi-permeable membrane on the bottom is provided. The membrane is optionally coated with laminin (1) by incubation. In step B, individual RPE cells (2) are placed in suspension on the membrane and incubated until they grow to confluence. In step C, the basal side of the membrane is populated with endothelial cells. In step D, a first layer of hydrogel (4) is applied to the RPE cell layer (2), which serves as a spacer layer. In step E, the retina organoid (5) is moved to the spacer layer (4) together with hydrogel. In step F, the final in vitro tissue culture (6) is formed, consisting of RO, embedded in hydrogel and disposed at a defined distance from the RPE and basal endothelium. Beginning at step F, the physiological maturation of the RO and the physiological interaction of photoreceptors of the RO with the RPE cells take place. In the embodiment shown, the retina organoid is perfused through the basal perfusion channel of the bioreactor through the endothelial and pigment epithelial layers.

Figure 4A:
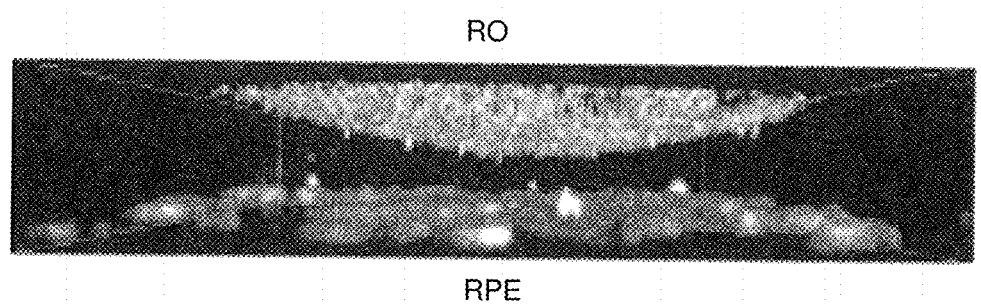
Figure 4B:
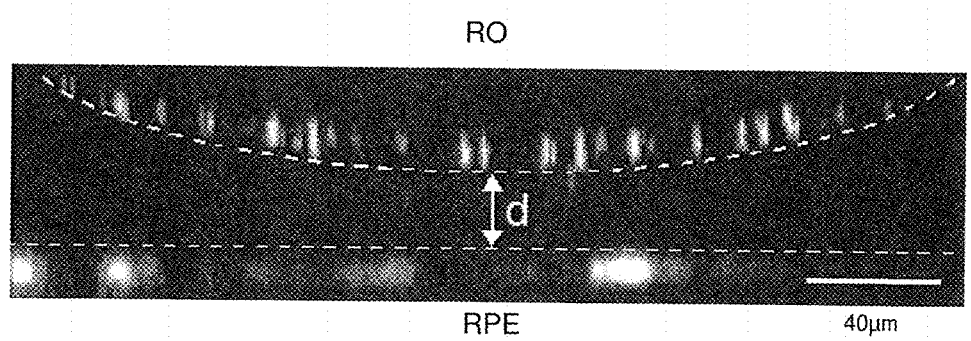

FIGS. 4A and B show "live cell imaging" with fluorophore-labeled iPS-RPE and iPS-RO, the outer segments of which were labeled with fluorophore-coupled PNA lectin (peanut agglutinin) (FIG. 4A). The defined positioning of the iPS-RPE tissue in relation to the iPS-RO is shown in FIG. 4B: Labeling of inner/outer segments of the iPS-RO using PNA lectin with subsequent co-cultivation with GFP-labeled iPS-RPE; the borders of the RPE (bottom) and the spheroid RO (top) are shown in dashed lines (scale: 40 µm, d=distance RO-RPE).

EXAMPLE MICROPHYSIOLOGICAL SYSTEM OF THE HUMAN RETINA (MPS)

1. Manufacturing/Assembling the Retina MPS

To produce the bioreactor, layers of the MPS are produced by molding polydimethylsiloxane (PDMS) on microstructured silicon wafers. However, the production of the MPS is not limited to this material, and other materials such as glass, PC and PET and combination thereof are possible. The microstructuring of the respective casting molds (master) is realized by UV lithography of photoresist (SU-8; MicroChem).

The endothelium/medium layer is molded using "exclusion molding" (EM). In the variant of the MPS with an additional media supply for the RO, the RPE fabric layer is also produced using EM.

The semipermeable membrane made of materials such as PET should have a pore size of 2 µm-3 µm and a thickness of 10 µm-30 µm. For the irreversible connection of PDMS and PET, the membrane is functionalized with bis-aminosilane from the liquid phase onto the membrane previously treated with oxygen plasma. This additional coating creates an irreversible connection between the membrane and the PDMS layers, which is later also treated with oxygen plasma.

The assembly of the MPS takes place in several steps. First, the molded endothelium/basal perfusion layer is placed on a support film on a glass slide having a thickness of 0.17 mm-1 mm after activation in the oxygen plasma and pressed on. To strengthen the connection, these are heated in a convection oven at 60° C.-80° C. The support film is removed from the endothelial/basal perfusion layer. The semi-permeable membrane and the RO & RPE tissue layer are applied in a plurality of steps. For this purpose, the through holes for the inlets and outlets are created in the layers below. The functionalized semi-permeable membrane is placed in the insert area provided for this purpose. As a last step, the RO & RPE tissue layer with the membrane is placed on the endothelium/basal perfusion layer and pressed on and heated to 60° C. to 80° C. for 10 hours-24 hours in a convection oven.

Several such bioreactor vessels can be arranged side by side in an MPS on a common support.

2. Establishment of Co-Cultivation in MPS

At the beginning, the assembled MPS is sterilized using an oxygen plasma with a power of 50 watts and an oxygen gas flow of 0.1 Nml/min-0.3 Nml/min and a treatment time of 5 to 15 minutes. The MPS can also be sterilized by autoclaving or gamma irradiation. After the plasma treatment has been carried out, the semipermeable membrane is coated in order to allow the RPE cells to adhere later.

For this, a 1:10-1:25 dilution of DMEM/F12 and laminin is applied and the MPS is incubated for 1 to 4 hours at 37° C. and 5% CO2 (FIG. 3A). Before the iPS-RPE cells are plated out, the excess laminin mixture is removed and the entire MPS is rinsed with medium. The previously separated iPS-RPE cells are added at a volume of 50-100 directly from above through the RO & RPE tissue chamber onto the membrane. iPS RPE cells are incubated for 30 to 60 minutes at 37° C. and 5% CO2 in order to allow the iPS RPE cells to adhere to the membrane (FIG. 3B). The iPS RPE cells were then cultivated externally in the MPS for a period of 1 to 3 days using syringe pumps at a constant medium flow of 10 µl/hour-20 µl/hour.

After the iPS RPE cells have grown confluently on the membrane, the iPS endothelial cells are introduced to the underside of the membrane (FIG. 3C). For this purpose, isolated iPS endothelial cells were injected into the endothelium/media channel and the MPS was placed on the head so that the cells sink to the bottom of the membrane. In order to allow the iPS endothelial cells to adhere completely to the membrane, the MPS was incubated for 30 to 60 minutes at 37° C. and 5% CO2. The MPS was then again supplied externally via a syringe pump at a flow rate of 10 µl/hour-20 µl/hour. After the iPS endothelial cells have covered the bottom of the membrane confluently, a hydrogel (in particular a hyaluron-based hydrogel) was introduced for precisely spacing the iPS-RPE cells relative to the individual iPS-RO (FIG. 3D). The hydrogel was injected directly through the RO & RPE tissue channel or through the upper opening of the respective RO & RPE tissue chamber in order to achieve a later distance between iPS-RPE and iPS-RO of 10 µm-50 µm. After the hydrogel had solidified completely, one iPS-RO each was applied to each bioreactor vessel directly from above (FIG. 3E). In order to prevent movement of the iPS-ROs for the duration of the cultivation, they were fixed using this hydrogel. The hydrogel is introduced by way of direct feed through the top of the RO & RPE tissue chamber.

The external medium supply to the MPS was then restored at a flow rate of 10 µl/hour-20 µl/hour. The MPS was then cultivated for a period of 1 to 7 days in order to track and analyze an interaction between RPE and photoreceptors of the ROs, and to investigate the influence of various active substances (FIG. 3F).

3. Use of the Retina MPS

The physiological functionality and vitality of the co-cultivation of the iPS-RO and iPS-RPE in the MPS was demonstrable as follows:

3.1 Vitality verification by way of "live cell imaging" with the aid of fluophore-labeled iPS-RPE and iPS-RO, the outer segments of which were labeled with flurophore-coupled PNA lectin (peanut agglutinin) (FIGS. 4A and 4B). Optical reconstruction using confocal microscopy was able to show an approximation and interaction of the two tissues in the MPS. Vitality of the different tissues for a cultivation period of up to 7 days.

3.2 Verification of maintenance of the tissue structure and assessment of the morphology by light microscopy and electron microscopy in the MPS: Both tissues had the expected phenomena and no signs of apoptosis or activation of glial cells could be found. In addition, the formation of large, outer segment-like structures was observed on the organoid side opposite the RPE (with the help of Peripherin2 and Rhodopsin as markers). These structures could not be detected on the side of the organoid facing away from the RPE or under a conventional organoid culture.

3.3 Immunohistological verification of typical retinal biomarkers: For the immunohistology of the iPS-RO, these were isolated from the MPS after the culture and sections were prepared. The immunohistology of the iPS-RPE cells was carried out directly in the MPS. The expression of the most important biomarkers of both iPS-RPE cells and iPS-RO (ZO-1, MiTF, RPE65, CHX10, ARR3, RHOD) were successfully shown.

3.4 Real-time quantitative PCR (qPCR) to verify the expression of typical retinal biomarkers: for this purpose, on the one hand iPS-RO which were co-cultivated with iPS-RPE cells or without iPS-RPE cells in the MPS were used after a period of 3 days. These were then compared with conventionally cultivated iPS-RO. A comparable expression of the corresponding markers at the mRNA level was successfully verified for all retinal cell types. Likewise, the iPS-RPE culture in the MPS was compared with the conventional culture and no significant differences in the expression of different RPE markers could be found.

3.5 Proof of the functionality of the co-cultivation of iPS-RO and iPS-RPE in the MPS using calcium imaging and phagocytosis assay: Spontaneous calcium flows within the photoreceptor cells could be verified, which indicates a physiological behavior of the photoreceptors in the MPS as well. Furthermore, the PNA lectin labeling of the outer segments also enables observation of physiological rejection thereof by the photoreceptor cell. The iPS-RPE not only showed an uptake and phagocytosis of externally-applied bovine outer segments in the so-called phagocytic assay, but also showed the uptake of these PNA-lectin-labeled outer segments in the MPS in live cell microscopy.

3.6 Establishment of Additional in-situ Measurement Methods in the MPS: CLARITY, a method for the optical clarification of tissue samples, was used to enable holistic immunohistological staining directly in the MPS. Typical retinal biomarkers were also verified using this method. Another method for observing iPS-RO in the MPS under real-time conditions is the use of reporter cell lines which have a fluorophore expression under the promoter of the activated marker gene for the corresponding cell type and thus enable live cell imaging within the MPS. This method can be used to detect photoreceptors, outer segments thereof, retinal ganglion cells and activated glial cells under real-time conditions.

3.7 Use of the MPS in medical drug testing: Medications with known retinopathic adverse drug effects were used for this. The anti-epileptic vigabtratin (VB), a GABA transaminase inhibitor, is one of these substances. The iPS-RO in the MPS were treated with VB for a period of 20 days for this purpose. No morphological change or activation of the glial cells in the iPS-RO could be verified. However, additional light exposure of the iPS-RO showed increased light activity after 11 days of VB treatment. In addition, acute VB treatment under light led to increased spontaneous calcium currents. This electrophysiological effect from the treatment with VB in the MPS thus provided evidence of the retinopathic side effects that are also observed in the patient. Also examined was the effect of chloroquine, a malaria drug with known retinopathic effects, which leads to so-called chloroquine retinopathy. Experiments with iPS-RPE cells under conventional cultivation conditions and in the MPS showed a vascularization which is due to a pathological enlargement of the lysosomes. This was successfully demonstrated by immunohistological staining of Lamp2 as a lysosomal marker. Finally, the effect of chloroquine on the iPS-RO in MPS was also examined. After 2 days of treatment of the iPS-RO, activation of the glial cells marked with the aid of a GFAP-promoter construct were observed.

The invention claimed is:

1. A method for the microphysiological co-cultivation of organoid tissue in a bioreactor vessel with a semi-permeable membrane on a bottom, the method comprising:
  (a) seeding cells of at least one first cell type onto the membrane;
  (b) cultivating the seeded cells to form at least one two-dimensional (2D) cell layer supported on the membrane; and
  (c) introducing into the bioreactor vessel on the at least one 2D cell layer: an organoid containing cells of at least two further cell types which are arranged in a defined three-dimensional (3D) structure relative to each other, and a hydrogel, wherein the organoid in the bioreactor vessel is spaced apart from the supported 2D cell layer by the hydrogel.

2. The method according to claim 1, wherein in step (c) the organoid in the bioreactor vessel is also spaced from walls of the bioreactor vessel by way of the hydrogel.

3. The method of claim 1, wherein in step (c) the organoid is introduced into the bioreactor vessel together with the hydrogel.

4. The method of claim 1, wherein step (c) contains the substeps of:
  (c1) introducing a portion of the hydrogel to form a defined spacer layer relative to the 2D cell layer and or to the 2D cell layer and the walls of the bioreactor vessel, and (c2) subsequently introducing the organoid on the hydrogel spacer layer formed.

5. The method according to claim 1, wherein in the cultivation of the 2D cell layer on the bottom of the semipermeable-membrane a basal pole thereof is perfused separately from an apical pole thereof.

6. An in vitro tissue culture in a bioreactor vessel with a semipermeable membrane on a bottom, the in vitro tissue culture comprising:
- a 2D cell layer containing at least a first cell type on the semipermeable membrane;
- an organoid containing cells of at least two further cell types which are arranged in a defined 3D structure relative to each other; and
- a hydrogel in which the organoid is embedded in the bioreactor vessel and which is spaced apart from a bottom 2D cell layer by a defined distance.

7. The in vitro tissue culture according to claim 6, wherein the defined distance of the organoid to the 2D cell layer is 1 to 100 μm.

8. The in vitro tissue culture according to claim 6, wherein the defined distance of the organoid to the 2D cell layer is 2 to 20 μm.

9. The in vitro tissue culture according to claim 6, wherein the organoid is embedded in the hydrogel so that the organoid is also spaced from walls of the bioreactor vessel.

10. The in vitro tissue culture according to claim 6, wherein a first 2D cell layer is disposed on a top of the membrane facing the organoid.

11. The in vitro tissue culture according to claim 10, wherein a further 2D cell layer is arranged on a bottom of the membrane facing away from the organoid.

12. The in vitro tissue culture according to claim 10, wherein the first 2D cell layer on the top of the membrane facing the organoid is at least partially comprised of epithelial cells.

13. The in vitro tissue culture according to claim 12, wherein a further 2D cell layer is arranged on a bottom of the membrane facing away from the organoid, and further wherein the further 2D cell layer on the bottom of the membrane facing away from the organoid is at least partially comprised of epithelial cells.

14. The in vitro tissue culture according to claim 6, wherein a cell type of the 2D cell layer is selected from a group consisting of:
- epithelial cells;
- epithelial-like cells;
- endothelial cells;
- stromal cells containing fibrocytes and/or fibroblasts;
- muscle cells containing myoblasts, myocytes and/or muscle fibers; and
- combinations thereof.

15. The in vitro tissue culture according to claim 6, wherein the organoid is selected from a group consisting of self-organizing multi-cell type tissues, and multi-cell type tissues with defined 3D structures which can be produced by cell pressure, containing: retinal organoids, brain organoids, pancreatic organoids, and intestinal organoids.

16. The in vitro tissue culture according to claim 6, wherein the organoid is a retina organoid which contains at least photoreceptor cells and cells of at least one other cell type of the neural vertebrate retina, and wherein the 2D cell layer is a confluent monolayer of retinal pigment epithelial cells.

* * * * *